United States Patent [19]

Wilkes

[11] 4,199,479
[45] Apr. 22, 1980

[54] HYDROGENATION CATALYST

[75] Inventor: John B. Wilkes, Richmond, Calif.

[73] Assignee: Chevron Research Company, San Francisco, Calif.

[21] Appl. No.: 881,084

[22] Filed: Feb. 24, 1978

[51] Int. Cl.$^2$ ............................................. B01J 29/00
[52] U.S. Cl. .................................................... 252/457
[58] Field of Search ....................................... 252/457

[56] References Cited

U.S. PATENT DOCUMENTS

| | | | |
|---|---|---|---|
| 1,555,539 | 9/1925 | Williams | 252/457 X |
| 2,077,409 | 4/1937 | Graves | 252/457 X |
| 2,109,884 | 3/1938 | Lazier | 568/885 |
| 2,110,483 | 3/1938 | Guyer | 568/885 X |
| 2,121,367 | 6/1938 | Schiller | 568/885 |
| 2,165,428 | 7/1939 | Waugh | 252/457 |
| 2,418,888 | 4/1947 | Kearby | 252/457 X |
| 2,782,243 | 2/1957 | Hess et al. | 568/855 |
| 2,810,764 | 10/1957 | Steadman et al. | 252/457 X |
| 3,173,959 | 3/1965 | Rittmeister | 568/885 |

FOREIGN PATENT DOCUMENTS

2256780  1/1975  France .
1131631 10/1968  United Kingdom .

*Primary Examiner*—O. R. Vertiz
*Assistant Examiner*—William G. Wright
*Attorney, Agent, or Firm*—D. A. Newell; John Stoner, Jr.; A. T. Bertolli

[57] ABSTRACT

A catalyst composition having an intrinsic surface area above about 60 square meters per gram as measured by the BET nitrogen adsorption method, said catalyst comprising from about 1 to 30 weight percent of a finely divided silica component, and from about 1 to 99 weight percent of a hydrogenating component comprising copper in either elemental or compound form and zinc oxide.

10 Claims, 1 Drawing Figure

HYDROGENATION CATALYST

BACKGROUND OF THE INVENTION

This invention concerns a catalyst composition and its preparation and use. In particular, this invention concerns a catalyst composition having a finely divided silica component and a hydrogenating component comprising copper and zinc oxide. The composition is an extremely active hydrogenation catalyst useful in the hydrogenation of esters to alcohols, particularly the hydrogenation of esters of glycolic acid to ethylene glycol.

The hydrogenation of esters to alcohols is well known. In general, the hydrogenation of an ester sometimes referred to as a reduction of the ester, is carried out using either a chemical reducing agent or a hydrogenation catalyst. The chemical reducing agents, such as lithium aluminum hydride, react through the hydride ion and are usually used in ether solution. However, for large scale laboratory or industrial preparations, the catalytic reduction of esters, under hydrogen pressure and increased temperature, is preferred. The most widely used catalyst is the so-called copper chromite catalyst (H. Adkins in Vol. VIII of "Organic Reactions", R. Adams, Ed., pp. 1-27, 1954).

A large amount of research effort has been expended in attempts to improve the catalytic hydrogenation process. In particular, various methods have been proposed for improving the catalyst composition to provide a more active hydrogenation catalyst. For instance, copper catalysts have been modified by the addition of other Group IIA or VIIA metals or their oxides, by the addition of activating substances, or by the use of a catalyst support.

U.S. Pat. No. 2,091,800 to Adkins et al discloses the use of a copper chromite/barium catalyst. Similarly, U.S. Pat. No. 2,093,159 to Schmidt discloses the use and combination of various catalytic metals and activating substances. According to the disclosure of U.S. Pat. No. 2,093,159:

"Suitable catalytic substances are for example copper, nickel, silver, zinc, cadmium, lead, or cobalt, or mixtures thereof and they may be prepared from their salts, oxides or other compounds prior to or after their incorporation with activating substances. The activating substances may be chosen from compounds of the metals giving acids with oxygen, such as chromium, molybdenum, tungsten, uranium, manganese, vanadium, or titanium or mixtures thereof as well as from compounds of the alkali, alkali earth or rare earth metals."

U.S. Pat. Nos. 2,109,844; 2,110,843; 2,118,007; 2,121,367; 2,782,243; 3,173,959; 3,267,157 and 2,285,448 disclose other combinations of hydrogenating metal catalysts and activators.

Although a wide variety of supports and modifiers have been used with copper hydrogenation catalysts, a limited number of types have found commercial acceptance. These are (1) copper chromite, with modification such as addition of BaO or $MnO_2$, (2) Cu-magnesia and (3) copper or copper oxide with zinc oxide. Copper-zinc oxide catalysts are commonly used for formation of alcohols by hydrogenation of esters or of aldehydes obtained by the "oxo" process. They are sometimes used for hydrogenation of the double bonds of fats. A typical example is contained in U.S. Pat. No. 2,305,104, where a Cu-Zn-Cr oxide catalyst is used for vapor phase hydrogenation of methyl glycolate (methyl hydroxyacetate) to ethylene glycol. They may also be used for methanol synthesis or for the reaction of carbon monoxide with steam to form hydrogen. For these reactions of carbon monoxide, the copper-zinc oxide catalysts are often modified with alumina or chromia.

Besides the use of activating substances and metal catalyst combinations, the use of an inert carrier or support is a common method used to improve catalyst performance. The support typically provides a large surface area on which the active component is spread out to give a larger surface area of active component, although it may serve other purposes as described by W. B. Innes in Chapter 6, Vol. 1 of "Catalysis", Paul H. Emmett, Editor, Reinhold, 1954.

Generally, large amounts of support are used relative to active component(s). Typically, supported catalysts will contain 40 to over 99 weight percent support.

Silica gel is a commonly used catalytic support. Its polularity is principally due to the presence of high-surface area silica having an abundance of surface hydroxyl groups. French Pat. No. 2,256,780 opened Aug. 1, 1975 describes a process for preparing a cupric catalyst with a silica-containing support. The process is characterized by the introduction of silica gel into a support consisting of hydrated copper (II) oxide applied to kieselguhr. U.S. Pat. No. 3,515,678 to Koritala also describes supported copper hydrogenation catalysts using either micronized silica or molecular sieve zeolites.

Silica-containing materials have also been used to promote catalytic activity by means other than supporting the active metal. For instance, British Pat. No. 759,426 describes promoted cobalt oxide catalysts of increased activity prepared by introducing colloidal silica or colloidal titanium into a purified aqueous cobalt nitrate solution. Similarly, U.S. Pat. No 3,652,458 to Gobron et al describes hydrogenation catalysts comprising nickel or copper deposited on a highly pure silica. The catalyst is formed by depositing the metal catalyst on silica in colloidal suspension.

SUMMARY OF THE INVENTION

An active and stable hydrogenation catalyst containing a minor amount of silica component and a select hydrogenating component has been found. The hydrogenating component comprises copper in either elemental or compound form and zinc oxide. Other first transition series metals, especially cobalt, may be present.

A further aspect of the invention is a method for preparing the catalyst comprising the steps of:

(1) admixing a copper salt and a zinc salt, and optionally, salts of cobalt, nickel or magnesium, with a hydrocolloid-forming silica and water to form a heterogeneous mixture; and (2) heating the mixture at a temperature of from about 100° C. to about 500° C. to dry and calcine the mixture.

BRIEF DESCRIPTION OF THE FIGURE

The following detailed description of the invention is more fully understood by reference to the accompanying FIGURE which graphically illustrates the relationship of catalyst pore volume as a function of the weight percent of silica in the catalyst.

DETAILED DESCRIPTION OF THE INVENTION

Among other factors the present invention is based upon the surprising effectiveness of a copper hydrogenation catalyst comprising from about 1 to about 30 weight percent of finely divided silica in combination with from about 1 to about 99 weight percent of a select hydrogenation component comprising copper in elemental or compound form and zinc oxides.

The catalysts may be used as a powder, pelleted, extruded, or supported upon or diluted by an inert material.

The silica component of the catalyst is a finely divided silicon oxide, i.e., silica. This component comprises from about 1 to about 30, preferably from about 5 to about 20, weight percent of the total catalyst weight when prepared in unsupported form. Silica exists in a variety of polymorphic crystalline forms as well as in amorphous modifications. Amorphous silica is substantially dehydrated, polymerized silica which may be considered as a condensation polymer of silicic acid. The preferred silicas for use in this invention are silicas capable of forming a hydrocolloid, i.e., colloidal silica, such as those commercially available under the trade names of Ludox(®) (Dupont) or Nalcoag(®) (Nalcoa). In these colloidal silicas, the silica particles are typically 5 to 60 nanometers in average diameter. Commercial silica sols usually also contain a trace of a cation, such as $NH_4+$, sodium or other alkali metal to stabilize the colloid. The preparation and properties of silica sols is described in the article by G. B. Alexander and R. K. Iler, J. Physical Chemistry, 57 932 (1953). An alternate, but less desirable form of silica is pyrogenic synthetic silicas. These are sold under the names of Aerosil(®) (Degussa) and Cab—O—Sil(®) (Cabot Corp.). The preparation and properties of pyrogenic silicas is covered in the Pigment Handbook, Vol. I, pp. 167–187) Wiley (1973). For use in the catalyst of this invention, relatively fine silica particles having a average diameter from about 4 to 60 nanometers are preferred, and silica particles having an average diameter of from about 5 to 30 nanometers are especially preferred.

The hydrogenating component of the catalyst of this invention comprises copper in elemental or compound form and zinc oxide. The hydrogenating component comprises from about 1 to about 99, preferably from about 70 to 95, weight percent of the total catalyst weight in unsupported form. The hydrogenating component can be formed by various methods. In a preferred method, an aqueous solution of a soluble copper salt and a soluble zinc salt, for instance the copper and zinc acetates or nitrates, is added to a base precipitating agent such as ammonium carbonate to form an aqueous slurry of the metal hydroxides, carbonates or hydroxycarbonates. The solids in the slurry are separated, for instance, by filtration or centrifugation, and reslurried. The solids are again separated to obtain a wet cake. This process is repeated until a low level of soluble impurities remains in the solids.

The silica component and hydrogenating component can be combined in several ways. For instance, the silica component can be incorporated into the hydrogenating component to form a silica modified catalyst by admixing the solid hydroxides, carbonates or hydroxycarbonates of the hydrogenating components with the silica component in aqueous suspension to form a slurry; drying the slurry and calcining the solids to form the oxides, and, if desired, compacting the powdered oxides to form the catalyst particles. In this method, care must be exercised to avoid the formation of substantial amounts of silica gel.

The silica component as a silica suspension in water, i.e., a silica sol, may be added at hydroxy carbonates stages during preparation of the hydrogenating component. For instance, silica sol can be added to the wet cake of the hydroxides, carbonates or hydroxy-carbonates of hydrogenating component to form a slurry or paste which is then heated to dry and calcine the solids forming a powdered precursor modified by incorporated silica. In an alternate embodiment of this process, the silica sol is added after the cake of insoluble metal salts is dried, and the resultant slurry or paste is dried and calcined to form the powdered catalyst. The heating step is preferably carried out in two stages. First, the wet cake is dried at from about 20° C. to about 150° C., preferably 100° C. to 120° C. Second, the dried cake is calcined at from about 200° C. to about 500° C., preferably 300° C. to 400° C. to convert the hydroxides, carbonates or hydroxycarbonates to the oxides.

The silica can also be incorporated by first acidifying the stabilized silica sol, and mixing it with the solution of the metal salts before precipitation of the hydroxides, carbonates, or hydroxy carbonates, much as described on page 2, lines 16–23, and lines 5–15 of British 759,426.

Another, but less desirable, method of incorporated silica is to mix pyrogenic silica, e.g., a Cab—O—Sil(®) with the metal salt solution before precipitating the insoluble metal derivatives.

The metals of the hydrogenating component of the fresh catalyst are present mainly as the metal oxides. Under hydrogenation conditions or before use, the copper, nickel or cobalt oxides may be partly or largely reduced to the elemental form. For convenience sake, the catalyst is generally described in terms of the metal oxide-form, that is, its precursor composition.

The catalyst can be used in supported or unsupported form. When used in supported form, the weight percent of support can be between 30 and 90 percent of the catalyst.

The effect of the silica modification is a surprisingly large increase in the activity of the catalysts when modified with 1–30 weight percent silica. At the same time, there is no loss in catalyst stability and suitability for continuous service, as would be expected for copper-silica catalysts.

Typical copper zinc oxide catalysts have a surface area of from about 30 to 60 square meters per gram ($m^2$/gram). In contrast, the catalyst of this invention has a surface area above about 60 $m^2$/gram. Thus, the surface area of the catalyst composition herein varies widely. In general, a satisfactory catalyst made by the process of this invention has a surface area in the range from about 80 to 300, and higher, square meters per gram. Preferred catalysts have a surface area in the range 100 to 300, preferably 110 to 200, square meters per gram.

The character and composition of the particles comprising the catalyst of the invention may vary widely depending upon the desired catalyst. In general, the particles are composed of silica and a hydrogenating component comprising the elemental metal, oxides, and complex salt forms of copper and zinc oxide with the proviso that the composition contain no more than about 30 percent by weight of the silica component.

Figure 1:
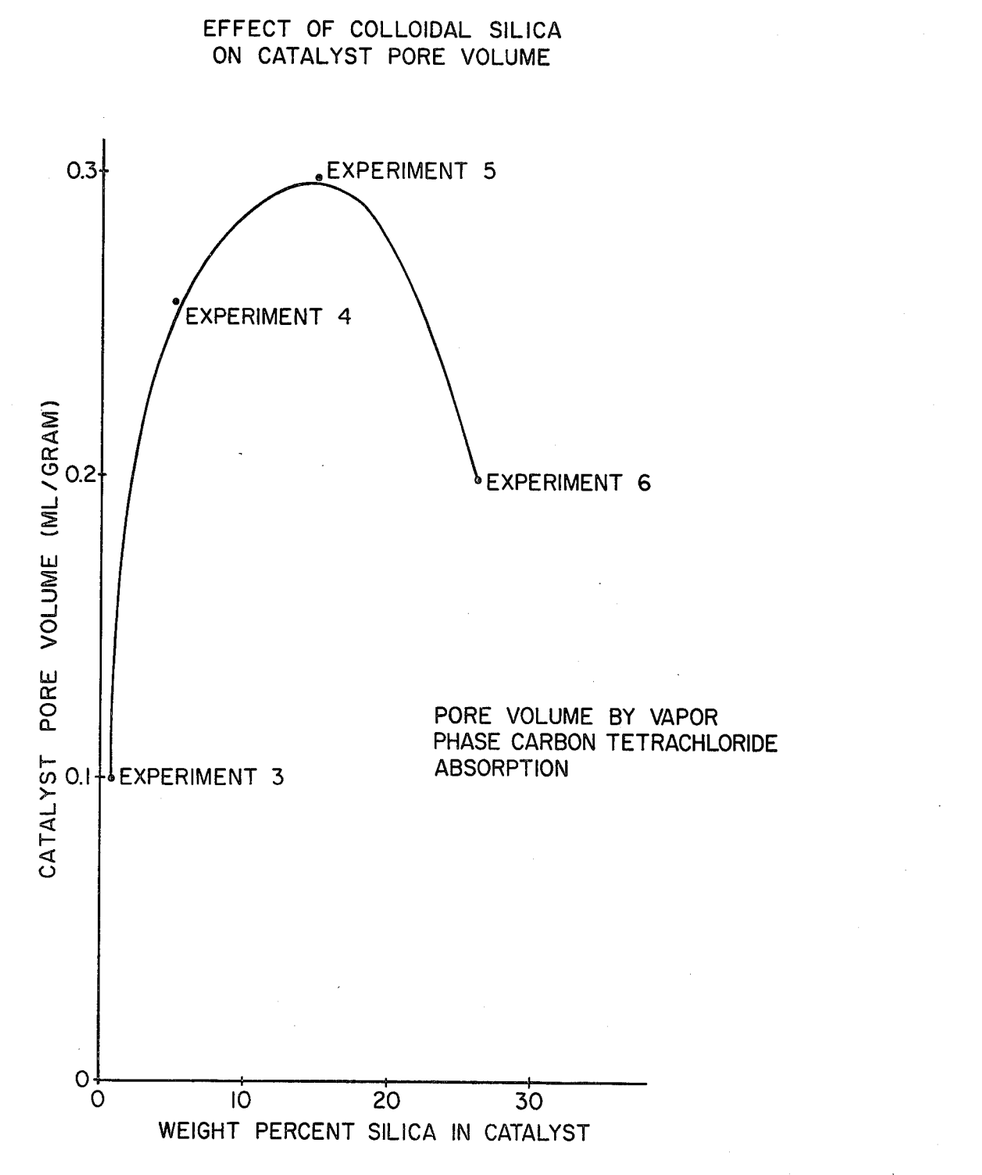

Referring to the FIGURE, it has been found that at above 15 weight percent of silica the effectiveness of the catalyst begins to decrease as does the catalyst pore volume and surface area.

The sizing of the particles in the compositon herein varies over a range. In general, a satisfactory catalyst is produced by the method herein when the crystals of the hydrogenerating component of the particles when measured after calcining and before reduction has an average diameter less than about 70, preferably less than about 50, Angstroms. Preferably, the particle sizing is diverse and of a wide range of average diameters. By average diameter as used herein is meant by definition the average diameter obtained by X-ray line broadening.

The catalyst may be extruded, tableted, or used as a powder depending upon the contemplated use, for example, as in fixed bed, fluid bed, or slurry reaction usage. Broadly, the more useful catalyst will be sized in the diameter range from about 0.5 mm to 15 mm, preferably 1 to 5 mm.

The catalyst of the invention is useful for the hydrogenation of any suitable feedstock. It is especially useful for the hydrogenation of aldehydes or esters, especially esters of glycolic and diglycolic acid, aliphatic monocarboxylic acid ester, aliphatic dicarboxylic acid diester, or alpha-hydroxy monocarboxylic aliphatic acid ester. The term "aliphatic" is used to include alicyclic, and ether linkages, e.g., as in an ester of alkoxy-acetic acid.

For the aliphatic acid esters, preferably the aliphatic groups are $C_2$ (including acetates) to $C_{30}$ and preferably they are saturated. The aliphatic groups may be both acyclic and cyclic. The other moiety of the ester (alcohol-derived moiety) is preferably a $C_1$ to $C_{20}$ alkyl group or alkyl hydroxy group such as from ethylene glycol or diethylene glycol. By the term "alcohol-derived moiety" is meant the group attached by ether linkage to the carbonyl group of the ester.

Preferred dialkyl oxalate ester feedstocks are those wherein the alkyl groups are $C_1$ to $C_{20}$, more preferably $C_1$ to $C_4$. Hydrogenation of the dialkyl oxalate yields ethylene glycol and alkyl monools.

Preferred aliphatic carboxylic acid ester feeds are of the formula wherein $R^1$ and $R^2$ are $C_1$ to $C_{20}$ alkyl groups or $C_1$ to $C_{20}$ hydroxy substituted alkyl groups, n equals 0 or 1 and A is an alkylene or oxaalkylene group of 1 to 10 carbon atoms which may be branched chain, and preferably is saturated with hydrogen.

The term "carboxylic acid esters" is used herein in the sense of esters composed of carbon, hydrogen, and oxygen and preferably not containing any halogen, sulfur or nitrogen.

The most preferred feeds for the process of the present invention are ethylene glycol glycolate, diethylene glycol glycolate, and polyglycolides and bis esters (typically the polyglycolide feeds are in the form of an alkyl glycolate obtained from the polyglycolide and solvent alcohol), e.g., $HOCH_2COOCH_2$—$COOR$ and, e.g., $HOCH_2COOCH_2CH_2OOCH_2OH$ and mixtures.

The ethylene glycol glycolate can be obtained from glycolic acid by reaction of ethylene glycol with glycolic acid or polyglycolides under usual esterification conditions. Likewise, the diethylene glycol glycolate can be obtained by reaction of glycolic acid with diethylene glycol. Both the monoglycolates and the bisglycolates of these glycol solvents, i.e., ethylene glycol and diethylene glycol, can be hydrogenated in the present process. Polyglycolide can be obtained by dehydrating glycolic acid, for example, by heating glycolic acid under vacuum and removing water.

Preferably, the process of the present invention is carried out in the presence of an alcohol or glycol solvent for the ester feed so that in the case of the polyglycolide feed the polyglycolide would be in the form of the ester resulting from the reaction of the alcohol or glycol solvent iwth the polyglycolide. Polyglycolide reacts with alcohols or glycol to form esters with less formation of water than would be the case in reacting glycolic acid directly with an alcohol. The general reaction for the polyglycolide with an alcohol solvent to form a glycolate is as follows:

Thus, in the case of n=5, there would be 5 mols of the glycolate for one mol of water.

Preferred solvents for the ester hydrogenation process of the present invention are $C_1$-$C_{20}$ alkyl alcohols. Ethylene glycol and diethylene glycol are especially preferred solvents. Lower alcohols such as methanol, ethanol, and propanol are also advantageous solvents. Higher alcohols such as isobutyl, n-butyl and higher boiling alcohols and glycols are preferred, as the water of reaction can be readily distilled from these alcohols and glycols, thus driving the equilibrium esterification reaction esssentially to completion. Preferred amounts of the alcohol solvent are 0.1–10 parts per one part ester feed by weight, more preferably 0.5–3 parts per one part ester feed. Preferably, the alcohol solvent is not an unsaturated alcohol nor an aromatic alcohol.

Although the reaction of the present invention may be carried out in mixed liquid-vapor phase, generally it is preferred to carry out the reaction with the ester and the solvent in the liquid phase. Typically, the hydrogen remains in gaseous phase except for dissolved hydrogen. Only small excesses of hydrogen are necessary. Large excess amounts of $H_2$ may be used to aid contacting and for cooling purposes.

Suitable pressures are between about 500 and 10,000 psig, preferably between 1000 and 5000 psig. Preferred hydrogenation reaction temperatures are 100° to 350° C., more preferably 180°–250° C. Suitable hydrogen to ester molar ratios are between 2/1 and 100/1, and preferably between 2.5/1 and 80/1. Suitable liquid hourly space velocities for the ester feed over the catalyst are between 0.1 and 50 and preferably are between 0.5 and 10.

EXAMPLES

The examples described below are presented to further illustrate the invention and are not intended to limit the scope of the following claims.

Example 1—Use of Ammonium Carbonate as Precipitating Agent

Two solutions, A and B, were prepared by the procedure summarized below.

| Solution A | 87.8 g | (Zn(OAc)₂ . 2H₂O (0.4 mol) | Dissolved in 2L 40° C. distilled water. |
| | 159.7 g | (Cu(OAc)₂ . H₂O (0.8 mol) | (Necessary to dissolve all Cu(OAc) . H₂O) |
| Solution B | 160 g | ammonium carbonate (1.4 mols) | Dissolved in 1800 cc distilled H₂O |

Solution A, the acetates, was added to the vigorously stirred Solution B, over a period of 45 minutes. After addition was complete, the mixture was stirred an additional 2 hours to complete precipitation. The mixture was filtered, and the filter cake washed by reslurrying in 1250 cc of distilled water 6 times. The cake was reslurried once again in 1250 cc distilled $H_2O$, and allowed to stand overnight. The cake was split into two batches of 184 g each.

35 g of Nalcoag 2326 (14.5% $SiO_2$, 5 nm particles, $NH_3$ stabilized) silica sol was added to one of the 184 g filter cakes, after diluting with 15 g $H_2O$. This formed a stiff paste. which thinned upon further mixing. The paste was dried over one weekend in a vacuum oven at 105° C. (Dried weight=52.38 g). The dried paste was ground and sized to pass through a 28 mesh screen and calcined in air at 150° C. for 2 hours; 200° C. for 2 hours; and 400° C. for 16 hours. The calcined weight of the silica modified catalyst was 41 g which is equivalent to about 12.3% incorporated $SiO_2$.

The silica modified catalyst was mixed with 3 weight percent graphite and 3/16″ diameter tablets were prepared. Average crush strength was 18.5 pounds, pore volume by $N_2$ adsorption was 0.388 cc/gram, and BET surface area was 113 m²/gram. A test of this catalyst (Example 13, Table I) showed it was substantially more active than a commercial $Cu.ZnO.Al_2O_3$ catalyst (Example 19) or $MnO_2$ modified copper-chromite catalyst (Example 20).

To illustrate the advantages of the catalyst of this invention, a control catalyst was prepared from the second portion of 184 grams of wet cake of the hydroxy-carbonates without addition of silica. A total of 34.6 g of catalyst was obtained. A pellet of this catalyst powder had a density of 3.06 g/ml while a pellet of the silica-modified catalyst had a density of only 1.92 g/ml.

Example 2—Use of Sodium Carbonate as Precipitating Agent 87.8 g of $Zn(OAc)_2.H_2O$, and 159.7 g of $Cu(OAc)_2.H_2O$ were precipitated as in Example 1, except using 127.2 g $Na_2CO_3$ instead of ammonium carbonate. The first filtration was a faint blue-green, pH=7.9. The second wash was colorless, pH=7.5; third, pH=7.3; fourth, pH=7.2; fifth, pH=7.3 (after sitting 3 days before filtering); sixth, pH=7.2; seventh, pH=7.1; and eighth, pH=7.1.

The filter cake was reslurried in 1250 cc distilled $H_2O$, and filtered using a 6″ perforated bowl centrifuge.

The centrifuged filter cake was mixed well with a solution of 75 g Nalcoag 2326 (14.5% $SiO_2$, 5 nm particles, $NH_3$ stabilized) and 40 g distilled $H_2O$. At first, this formed a very stiff paste, which thinned upon further mixing. The paste was dried over the weekend, in a vacuum oven under house vacuum with a small bleed of $N_2$, at 110° C. (Dried weight = 136.19 g). 3.0 g of the dried catalyst was retained and the remainder was ground to pass through a 28 mesh screen and calcined in air at 150° C. for 2 hours; 200° C. for 2 hours, 400° C. for 18 hours. (Calcined weight=102.17 g). The catalyst was brown-black rather than black which is usual case when $NH_4Co_3$ precipitated and contains approximately 10.4% $SiO_2$.

A portion of calcined catalyst was mixed with (3%) graphite and pelleted as in Example 1. The catalyst density was 2.55 cc/g, and the pore volume was 0.197 cc/gram by $N_2$ absorption. BET surface area was 55 m²/g.

The fundamental change in the catalysts cause by modification with silica can be shown by examination of crystallite size by X-ray line broadening. This technique is thoroughly described in the book "Structure of Metallic Catalysts", by J. R. Anderson, Academic Press, 1975, pp. 365-368. As described there, X-ray line broadening is particularly applicable to metal crystallites of size 3.0-5.0 nm (30-500 Angstroms). Below 30 Angstroms, the X-ray diffraction line is so broad and diffuse as to disappear.

Using a recording diffractometer, the catalysts in Examples 1 and 2 were examined for crystallite size with the following results.

| | | Average Crystal Dia., Angstrom | |
|---|---|---|---|
| Example | % $SiO_2$ | ZnO | CuO |
| Control | None | 120 | 130 |
| 1 | 12 | <50 | ≅50 |
| 2 | 10 | ≅70 | ≅60 |

The results show the great effect of $SiO_2$ on particle size, and that precipitation of the carbonates with $Na_2CO_3$ (Example 2) decreases the effect. The effect of colloidal silica is greater than indicated by the numbers above, as X-ray line intensities are very low in spectra from the modified catalysts in Examples 1 and 2, showing that most of the ZnO and CuO crystals are too small to be detected (<30 Angstroms).

Examples 3-6—Cobalt-Copper-Zinc Oxide Catalysts

Example 3 illustrates for comparative purposes a cobalt-copper-zinc oxide catalyst which is not modified by the incorporation of silica.

Examples 4-6 illustrate cobalt-zinc-copper oxide catalysts, modified with different amounts of colloidal silica.

Example 3—(No silica)

1500 ml water; 60 g of copper diacetatemonohydrate, (0.3 g mol); 75 g of cobalt diacetate tetrahydrate, (0.3 g mol); and 66 g of zinc diacetate dihydrate, (0.3 g mol) were added to a 2-liter beaker. The mixture was stirred until the salts were dissolved.

120 g of ammonium carbonate (about 1.17 mols) was dissolved in 1500 ml of water in a 4-liter beaker. The solution of metal salts was added dropwise, with stirring to the ammonium carbonate solution. After addition was complete, the slurry was stirred an additional 2.5 hours. The mixture was filtered, and the filter cake reslurried 4 times with one liter of water and filtered. The slurry was dried in a vacuum oven overnight. The dried slurry was calcined in air 2 hours at 100° C., 2 hours at 200° C., and 16-18 hours at 250° C. 5 weight percent dry, powdered sodium metasilicate was added as a binder (otherwise pelleting is unsatisfactory). 3 weight percent graphite was added as a lubricant. The mixture was pelleted and the pellets were ground and screened to 20-28 mesh. A test of the activity of this catalyst is shown in Example 14, Table I.

Example 4 (4-5% Silica)

Approximately 5% $SiO_2$ based on final catalyst weight was added to a precipitated metal carbonate slurry as summarized below. The silica sol was DuPont Ludox AS, which was 30 weight percent $SiO_2$ having a particle size of 13 to 14 nm, and a surface area of 210-230 $m^2/g$ with 120 $SiO_2$/1 $NH_3$ by weight.

Procedure:

| Solution A | 48.0 g | $Cu(OAc)_2 \cdot H_2O$ (0.24 mol) | Dissolved in 1000 ml water. |
|---|---|---|---|
| | 60.0 g | $Co(OAc)_2 \cdot 4H_2O$ (0.24 mol) | |
| | 52.8 g | $Zn(OAc)_2 \cdot H_2O$ (0.24 mol) | |
| Solution B | 96.0 g | $(NH_4)_2CO_3$ (1.0 mol) | Dissolved in 800 ml water |

Solution A was added at a fast dropwise rate to Solution B while vigorously stirring. When the addition was complete, (pH#7), stirring was continued for an additional 30 minutes. Then, 8 g of Ludox AS, diluted to 25 cc with water, was added slowly to the stirred carbonate salt mixture. The mixture was then stirred for 2 hours, and liquid was filtered off. The filter cake was washed with water three times. The washed filter cake was dried overnight in vacuum oven at 103° C. The dried precipitate was calcined at 2 hours at 150° C.; 2 hours at 200° C.; and 19 hours at 400° C. The calcined catalyst weighed 52.91 g.

25 g of the calcined catalyst was compressed into ⅜" OD pellets using a Pasadena hydraulic press. Pellets were compressed by placing approximately 2 g powder into die and pressing to 10,000 pounds ram force, 4" ram, and holding there for 3 minutes. The pellets were crushed and sized to 14-28 mesh. A test of this catalyst (Example 15, Table I) showed that it was slightly more active at 420° F. than the silica-free catalyst was at 425° F. (Example 14). The BET surface area and catalyst pore volume were increased by addition of silica as shown in Table I.

Example 5—(15% Silica)

Co-Zn-Cu carbontes prepared exactly as in Example 4 except that washing was begun two hours after the addition of acetates were completed. The filter cake was washed twice before allowing to stand overnight in the third wash. The washed filter cake was slurrid and washed and filtered four additional times with 2.5 L water, and reslurried with 2.5 L water. The catalyst was filtered using a 6" perforated bowl centrifuge and parachute cloth as a filter. The resulting cake was broken up, stirred (wet weight=1033) and split into 3 equal batches of 344 g each. One batch was mixed with 42 g Ludox AS, undiluted. As in Example 4, a very stiff paste formed, but the paste grew less and less stiff as it was mixed, until after approximately 15 minutes of stirring, it would not hold a peak and would flow until level.

The batch was then dried in a vacuum oven overnight at 110° C., with a slight nitrogen bleed to sweep away water vapors. The dried catalyst was calcined at 150° C. for 2 hours; 200° C. for 2 hours; and 400° C. for 19 hours. The calcined catalyst was mixed well with 3% graphite, and pelleted on a Stokes double pressure tableter, using a 3/16" die. Pellets were approximately 2 mm high. The pellets were crushed and screened for catalyst testing. The results of the test are shown in Example 16, Table I. It can be seen that this catalyst is about as active at 380° F. as the catalysts of Examples 13 and 14 were at 425° F. and 420° F. The surface area of the Example 16 catalyst is about twice that of the control (Example 14) and the catalyst pore volume is 2.7 times as great as that of the control catalyst.

Example 6—(26% Silica)

A batch of Co-Zn-Cu carbonate was prepared as in Example 5. The wet filter cake weighed 1281 g. 4/5 of the cake, 1024 g, was dried overnight, at 105° C. in vacuum oven. Dried weight=278.5 g.

69.6 g of dried cake, ground to pass through a 28 mesh screen, was mixed with 124 g Nalcoag 2326 silica sol (14.5% $SiO_2$, 5 nm particles, $NH_3$ stabilized). The mixture was very thin at first, after approximately 2-3 minutes of mixing, the sol was either absorbed into catalyst granules, or coagulated as the mixture set up (like a dry mix of cement). The dry mixture was broken up into ⅛-¼" chunks, and heated overnight in a vacuum oven at 105° C. (Weight=81.91 g). The resulting material was ground to pass through a 28 mesh screen and calcined at 150° C. for 2 hours, 200° C. for 2 hours, 400° C. for 19 hours. The calcined weight 68.66 g which corresponds to 26.2% $SiO_2$.

The day that the catalysts were pelleted was a very dry day. Since the tablets were unexpectedly weak and friable, the catalyst powders and graphite were placed in a humidor (made by placing water in dessicator) and covered and let stand for 7 days. The pellets that were made from the humidified catalyst were stronger, less friable, and more dense. Crush strength ranged from 22.8 to 39.8 pounds and averaged 31.6 pounds. The average pellet density was 2.18 cc/g. A test of this catalyst is shown in Example 17 (Table I). At 400° F. the catalyst was more active than the control catalyst (Example 14) was at 400° F. However, it was not as active at 380° F. as the catalyst containing 15% silica (Example 16).

Examples 7-9

Example 7 illustrates for comparative purposes a copper catalyst modified by silica, but not containing zinc in the hydrogenating component. Example 8 illustrates for comparative purposes a copper-zinc-aluminum catalyst.

Example 7—Cu-Silica Catalyst, No ZnO

With vigorous stirring, an acetate solution (199.6 g $Cu(OAc)_2.H_2O$ (1 mol) dissolved in 2500 cc 25° C. distilled water) was dropped, at a rapid rate into a carbonate solution (102 g amonium carbonate dissolved in 1500 cc distilled water) precipitating cupric hydroxy carbonate, over a period of 45 minutes. Stirring was continued for an additional two hours to insure complete precipitation. The mixture was allowed to stand over the weekend.

The blue precipitate was filtered. The filtrate was an intense blue. The blue filter cake was washed by reslurrying in 200 cc distilled water and filtering 5 times. Each wash was less blue until the final two washes were colorless. While filtering the final time, the filter cake changed from blue to green; what was a nearly dry cake turned to a gel-like mass. When stirred, it turned into a slurry. An additional amount of clear liquid was filtered from it. The cake was then dried as much as possible on funnel cake=165.88 g. and spirit into two batches of 82.9 g each.

One batch was mixed very well with 19.0 g Nalcoag 2326 (14.5% $SiO_2$, 5 nm particles, $NH_3$ stabilized). This was added in increments, and was the maximum that could be added without the slurry becoming too thin.

The mixture was dried overnight at 105° C. in vacuum oven. (Dried weight=49.87 g). The dried mixture was ground to pass through a 14 mesh screen and calcined at 150° C. for 2 hours; 200° C. for 2 hours; 400° C. for 17 hours. (Calcined weight=37.01 g). $SiO_2$ content was 7.4%. The density of a ⅜" tablet was 2.74 cc/g. A test of this catalyst (Example 20, Table I) showed a high initial activity, but the catalyst disintegrated rapidly.

Example 8—Cu-Zn-Al Oxide Catalyst

In accordance with British Pat. No. 1,131,631, two solutions, described below, were prepared.

| Solution A | 69.4 g | $Cu(NO_3)_2 \cdot 3H_2O$ (0.287 mol) | Dissolved in distilled water to make 400 cc |
| | 132.3 g | $Zn(NO_3)_2 \cdot 6H_2O$ (0.445 mol) | |
| | 85.3 g | $Al(NO_3)_3 \cdot 9H_2O$ (0.227 mol) | |
| Solution B | 340.0 g | $NaCO_3$ (3.21 mol) | Dissolved in distilled water to make 2000 cc |

Carbonate Solution B was placed in a 4-liter beaker and heated to 77° C., while being agitated by a Gifford-Wood high shear stirrer. Solution A, the nitrates, was heated to 75° C., and was added to the very vigorously agitated carbonate solution over 2 minutes. The pH of the mixture at the beginning of addition was 7.7 (pH of $Na_2CO_3$ solution at 78° C.=8.8). The pH 2 minutes after addition was 8.2. The pH 6 minutes after addition was 8.4. The pH after 10 minutes after was 8.41.

1000 cc distilled $H_2O$ was added, the mixture was heated to 90° C., and held for 1 hour while stirring (pH, 0 time at 90° C. was 8.3; at 15 minutes was 8.5; at 25 minutes was 8.7; and at 1 hour was 8.7). The mixture was filtered and the filter cake was reslurried in 2000 cc distilled $H_2O$ and refiltered. The filter cake was then reslurried in 3000 cc $H_2O$ and dried over the weekend at 120° C. (Dried weight was 103.75 g). The product was calcined at 300° C. for 8 hours; (calcined weight was 80.3 g). The calcined catalyst was ground to pass through a 14 mesh screen.

50 g of the catalyst powder was throughly mixed with 1.5 g (3%) of graphite and was pelleted on a Stokes dual pressure press using a 3/16" die. Pellet density of 3/16" pellets was 2.06 cc/g. A test of this catalyst is described in Example 19.

Example 9

In this example, an attempt was made to improve a copper chromite catalyst by silica modification. Instead of the catalyst becoming easier to pellet, it became more difficult to pellet. Also, there was little effect on pellet density. This demonstrates that colloidal silica does not improve all copper-containing catalysts.

The following procedure was followed to determine if the addition of colloidal silica to copper chromite catalyst before ignition would improve the catalyst in a manner similar to its effect on Cu-ZnO and Cu-Co-Zno catalysts. The procedure used to make the catalyst was that described in "Organic Synthesis", Collective Vol. II, pp. 142–145, except for ignition technique and the omission of barium nitrate.

| Solution A | 241.6 | $Cu(NO_3)_2 \cdot 3H_2O$ (1.0 mol) | was dissolved in 800 cc distilled water. |
| Solution B | 126.0 g | $(NH_4)_2Cr_2O_7$ (0.5 mol) | Was dissolved in 600 cc distilled water and then 150 cc 28% aqueous ammonia was then added to give a solution of $(NH_4)_2CrO_4$. |

Solution B was added to Solution A (copper nitrate) in a thin stream from a dropping funnel over a period of 15 minutes while stirring vigorously. The mixture was stirred for an additional 15 minutes after which the reddish-brown copper ammonium chromate was filtered from the deep green mother liquor. The filter cake was reslurried twice in 1000 ml $H_2O$ and filtered. The mixture from the second reslurry was filtered using a 6-inch perforated bowl centrifuge. The 352 g filter cake was split into two batches of 176 g each.

One batch was mixed with 66 g Nalcoag(®) 2326 (14.5% $SiO_2$, 5 nm particles, $NH_3$ stabilized). This formed a stiff paste which thinned upon mixing to a very liquid mixture that had too much supernatant liquid to give a homogenous mass when dried.

Since the silica sol added left too much supernatant liquid, the following preparations were carried out using more concentrated silica sol or less silica sol.

Procedure: The same procedure as above was followed except the batch size was doubled. The filter cake was washed with 1000 cc distilled water and reslurried in 1250 cc distilled water and filtered in 2 batches using a 6-inch perforated bowl centrifuge. The filtered material (755 g of wet precipitate) was split into 5 batches, A–E, each weighing 151 g.

Batch A—control, no additive. Dried at 110° C., vacuum oven, overnight weight=77.95 g.

Batch B—mixed with 9.0 g Ludox(®AS-40 (40% $SiO_2$, 21 nm particles) and 11 cc water dried at 110° C. in a vacuum oven overnight, Weight=75.25 g.

Batch C—mixed with 18.1 g Ludox AS-40 plus 4 cc water. Dried at 110° C. in a vacuum oven overnight, Weight=81.07 g/

Batch D—mixed with 19.5 g Nalcoag 1034A (34% $SiO_2$, 16 to 22 nm particles, acid stabilized) plus 5 cc water. Dried at 110° C. in a vacuum oven, overnight. Weight=78.34 g.

Batch E—mixed with 220 g Nalcoag 2326 (14.5% $SiO_2$, 5 nm particles) plus 2 cc water. Dried at 110° C. in a vacuum oven, overnight. Weight=78.34 g.

2.0 g of each batch were retained before calcining. All five batches were broken up into approximately ¼–½" chunks (leaving in chunks is advisable as lumpy conditions diminishes spraying of the chromite on ignition), and calcined at 200° C. for 30 minutes; 250° C. for 30 minutes; 300° C. for 30 minutes; 350° C. for 30 minutes; and 400° C. for 60 minutes.

Batch A, control, calcined weight=61.14 g.

Batch B, 9.0 g Ludox As-40, calcined weight=58.33 g, 6.0% $SiO_2$.

Batch C, 18.1g Ludox AS-40, calcined weight=64.22 g, 11.0% $SiO_2$.

Batch D, 19.5 g Nalcoag 1034A, calcined weight=63.68 g, 10.2% SiO$_2$.

Batch E, 22.0 g Nalcoag 2326, calcined weight=60.90 g, 5.1% SiO$_2$.

4 g of each batch was mixed with 0.12 g graphite, and two ⅜" tablets were pressed at 10,000 pounds ram force, 4" ram holding pressure for 3 minutes. Batches B, C and D, made with Ludox As-40 and Nalcoag 1034A, fell apart in layers while removing from die.

Batch A—control, gave a pellet with a density of 2.11 g/cc. The tablet appeared fairly strong. Batch E containing Nalcoag 2326 gave a pellet with a density of 1.96 g/cc. The tablet had cracks around circumference, appeared weak and about to split into layers. In contrast to the copper-zinc oxide or cobalt-copper-zinc oxide catalysts, the addition of silica made the catalyst pellets weaker, instead of stronger. The silica had little effect on the density of the catalyst pellets.

Example 10

In this example, silica was incorporated by acidifying the alkaline, stabilized colloid, adding to the metal salt solution, and precipitating the hydroxy carbonates. More of the soluble metal salts were lost, but a good catalyst resulted.

The silica sol was acidified and added to the solution of metal acetates, and this mixture was precipitated by addition to ammonium carbonate solution. The technique resembles that in British Pat. No. 759,426, page 2, lines 16–18, but used more SiO$_2$ and less HNO$_3$. Three solutions, A–C, were prepared as follows.

| Solution A | 240 g Cu(OAc)$_2$ . H$_2$O (1.2 mols) | Dissolved in 6 liter distilled water. |
|---|---|---|
| | 300 g Co(OAc)$_2$ . 4H$_2$O (1.2 mol) | |
| | 264 g Zn(OAc)$_2$ . 2H$_2$O (1.2 mol) | |

Solution B: 285 g, of Nalcoag 2326 (14.5% SiO$_2$, 5 nm particles, NH$_3$ stabilized) was added to 750 cc distilled H$_2$O, and then was acidified, with vigorous stirring, by adding rapidly 9.0 g of 70% HNO$_3$ to give approximately a mixture about 0.1 N in HNO$_3$.

Solution C: 480 g, of ammonium carbonate dissolved in 6 L distilled water.

Solution A was added, with vigorous stirring, to Solution B, and this mixture was added at a rapid dropwise rate to Solution C with vigorous stirring. After approximately 10% of the addition was complete, the metal acetate-silica sol mixture started to cloud with a fine precipitate. Addition was stopped and the mixture acidified to pH 3.4 with 45 cc 70% HNO$_3$. After 80–85% addition, the pH of the metal hydroxy carbonate slurry was 6.5. 100 g additional amonium carbonate was added, (pH=7.1) and addition of Solutions A+B was completed (total addition time 2¾ hours). The pH of the slurry was 6.9.

After addition was completed, stirring was continued for two hours to complete precipitation. The mixture was then filtered, the filtrate being an intense blue. The filter cake was reslurried in 2.5 L distilled H$_2$O and filtered. This was repeated two times, but reslurrying was difficult so the cake was split into two batches, each washed by reslurrying in 2.5 liters H$_2$O and filtering. This was repeated 4 times until wash came out colorless. The filter cake (1691 g) was broken up and dried, under vacuum, at 105° C. for 65 hours (Dried weight=337.3 g).

337.4 g of the dried cake was ground to pass through a 28 mesh screen. Although there was some obvious loss while crushing, the 28 minus mesh powder weighed 341.7 g when it ws put into muffle furnace for calcining. This is attributed to the fine powder picking up atmosphere moisture. The ground catalyst was calcined at 150° C. for 2 hours, 200° C. for 2 hours, 400° C. for 17 hours (Calcined weight=279.6 g).

Two ⅜" diameter tablets were pressed, at 10,000 pounds platen pressure, held for 3 minutes. The density was 1.77 g/cc. The tablets were crushed to 14×28 mesh, pore volume, measured by CCl$_4$ absorption, was 0.316 cc/g.

100 g of the catalyst was mixed very well with 3 g of 325 mesh graphite and pelleted with a 3/16" die in a Stokes double pressure tableting machine. Pellet density (measured with vernier calipers) was 1.73 g/cc. The pellets had an average crush strength of 21.8 pounds. A small amount of pellets were sized to 14 to 28 mesh.

The catalyst contained 11.5% SiO$_2$ measured by neutron activation; and 26.1% Co$_3$O$_4$; 23.7% CuO; and 25.7% ZnO, as measured by X-ray fluorescence. The crushed catalyst was tested for activity as shown in Example 21, Table I. The activity compared favorably with that of the catalyst used in Example 16. The activity was greater at 380° F. than that of the unmodified catalyst at 425° F. (Example 14).

Example 11

Aqueous colloidal silica has been found to greatly modify Cu-Zn oxide or Co-Zn-Cu oxide catalysts. Usually the silica has been added to the hydroxy carbonates, although in some instances the acidified silica sol was added before precipitation and was effective.

In this example, fumed dry silica was examined. The material tested was Cab-O-Sil (®), MS, BET surface area=256 m$^2$/g. Particle size was 14 microns, per manufacturer's literature.

The following Solutions A and B were prepared as in previous examples.

| Solution A: | 99.6 g Co(OAc)$_2$ . 4H$_2$O (0.4 mol) | Dissolved in 2000 cc distilled water. |
|---|---|---|
| | 87.8 g Zn(OAc)$_2$ . 2H$_2$O (0.4 mol) | |
| | 79.9 g Cu(OAc)$_2$ . H$_2$O (0.4 mol) | |

After the acetates dissolved, 10.0 g Cab-O-Sil (®) MS was dispersed into the solution using a "Dispersator", manufactured by Premier Mill Corp., and stirring at high speed for 10 minutes.

Solution B: 160 g, ammonium carbonate dissolved in 1800 cc distilled water.

Solution A, the acetate and Cab-O-Sil (®), was added with vigorous stirring to Solution B, the carbonate, at a rapid dropwise rate over a period of 40 minutes. During this time, the Cab-O-Sil settled to a very small degree. After addition was complete, the mixture was stirred for an additional two hours to complete precipitation. The filtrate was intense blue. The filter cake was washed by reslurrying in 2000 cc distilled water and filtering 6 times. Each wash was progressively lighter in color, last two washes were colorless. The cake was dried overnight in vacuum oven at 108° C. (Dried weight=123.77 g). The dried cake was ground to pass through a 14 mesh screen and calcined at 150° C. for 2 hours, 200° C. for 2 hours, and 400° C. for 17 hours (Calcined weight=94.53 g). The calcined catalyst contained 10.6% fumed silica. A ⅜″ tablet had a density of 2.08 g/cc. The pore volume by vapor phase absorption of $CCl_4$ was 0.267 cc/g. The pore volume is considerably increased over the pore volume of 0.139 cc/g for the unmodified catalyst (Example 13, Table I), but is less than the pore volume of 0.286 cc/g found with only 5% silica in Example 14, Table I. This shows that this method of adding silica is effective in improving catalyst properties, but is less effective than the use of colloidal silica suspension (See FIG. 1).

EXAMPLE 12

This example shows that colloidal silica of larger particle size is effective in this invention, even though this type of silica is not preferred.

A fresh batch of Co—Cu—Zb hydroxy carbonates was prepared as described in Example 5 to give 1252 grams of wet cake. 250 grams of this wet cake was mixed with 25 g of Nalcoag 1060 silica sol (50 weight percent silica, average particle size 50-70 nm, surface area 40-60 m²/gram, stabilized with about 0.25% $Na_2O$). The mixture was dried in a vacuum oven at 105° C. and calcined at a maximum temperature of 400° C. The final $SiO_2$ content was 19.5 weight percent.

a ⅜″ pellet was prepared from this catalyst powder in the manner previously described. The pellet had a density of 1.99 g/ml. After crushing, the catalyst was found to have a pore volume of 0.263 ml/gram, by usuing $CCl_4$ absorption as described by Benesi et al, Analytical Chemistry, Vol. 27, pages 1963-1965 (1955).

The results show substantially lower density and higher pore volume than for the unmodified catalyst (Example 3).

Examples 13-22

In these examples, various catalysts were examined for hydrogenating activity. Example 13 is a control, Examples 14-17 and 21 illustrate catalysts of this invention. Examples 18-20 are similar to the catalyst of this invention and are included for comparative purposes. Table I summarizes the catalyst properties and results.

The copper and cobalt (if present) component of the catalyst were reduced in hydrogen before starting hydrogenation of the ester feed. The reduction of the catalyst should be carried out in such a manner as to avoid temperatures above 275° C. in the catalyst bed. These techniques are well known, the conditions required depending largely on the size of the catalyst bed, and provisions for removing the heat of reaction. (German Pat. No. 2,650,443 thoroughly describes catalyst reduction techniques for $CuO$-$ZnO$-$Al_2O_3$.)

Hydrogenation— All of the examples were carried out with 47-52% ethylene glycol glycolate in ethylene glycol. Concentrations of ester were determined by saponification number. Analysis of feeds as acetate esters by gc showed significant amounts of bis esters were actually present. The results shown in Table I are all at 1500 psig, 3.2 LHSV, except as noted.

TABLE I

EFFECT OF COLLOIDAL SILICA ON CATALYST PROPERTIES AND ACTIVITIES

| | Active Components | | Properties Pelleted Catalyst[1] | | | Activity Test, Continuous Pilot Plant[2] | | | |
|---|---|---|---|---|---|---|---|---|---|
| Ex. No. | Type (as Oxides) | Mol Ratio | Silica Wt. % | Surface Area, m²/g | Pore Vol. cc/g. | Run No. | Temp. °F. | Ester Conversion Mol % | Total Catalyst Service, Hours | Grams Catalyst |
| 13 | Cu—Zn | 2/1 | 12 | 113 | 0.388 | 11 | 400 | 98 | 20 | 4.1 |
| | | | | | | | 360 | 96 | 44 | |
| 14 | Co—Cu—Zn | 1:1:1 | None | 91 | 0.139 | 1 | 425 | 95 | 307 | 8.5 |
| | | | | | | | 410 | (82)[5] | | |
| 15 | Co—Cu—Zn | 1:1:1 | 5 | 140 | 0.286 | 7 | 420 | 97 | 19 | 5.4 |
| | | | | | | | 380 | 78 | 43 | |
| 16 | Co—Cu—Zn | 1:1:1 | 15 | 179 | 0.382 | 8 | 400 | 98 | 24 | 4.6 |
| | | | | | | | 381 | 94 | 48 | |
| | | | | | | | 360 | 86 | 72 | |
| 17 | Co—Cu—Zn | 1:1:1 | 26 | 155 | 0.256 | 9 | 400 | 98 | 24 | 5.6 |
| | | | | | | | 380 | 84 | 63 | |
| | | | | | | | 360 | 71 | 49 | |
| 18 | Cu | — | 7 | | | 19 | 400 | 99 | 18[3] | |
| 19 | Cu—Zn—Al | .29/.45/.23 | None | 57 | 0.218 | 20 | 380 | 3 | 6 | 5.4 |
| 20 | Cu—Cr—Mn[4] | 38/31/3 | None | 59 | 0.156 | 15 | 400 | 71 | 20 | 6.0 |
| | | | | | | | 425 | 89 | 27 | |
| | | | | | | | 425 | 67 | 50 | |
| 21 | Co—Cu—Zn | 1/1 | 11.5[6] | 149 | 0.390 | 10 | 380 | 98 | 47 | 4.6 |
| 22 | Cu—Zn—Al | .33/.65/.02 | None | 25-40 | | 26 | 420 | 46[7] | 38 | 6.7 |

[1]In unreduced (oxide) form. Surface area - BET. Pore volume $N_2$ at p/po = 0.98.
[2]5cc 14-28 mesh crushed pellets, 1500 psig; LHSV 3.2; 48-52% ethylene glycol glycolate in ethylene glycol.
[3]Catalyst disintegrating.
[4]$MnO_2$-promoted copper chromite.
[5]LHSV 2.4 instead of 3.2.
[6]Added, acidified, to metal salt solution, before precipitating.
[7]Test run at LHSV of 1.6 instead of 3.2. (United Catalysts C 61-1-01 catalyst)

What is claimed is:

1. A catalyst composition having a BET intrinsic surface area above about 60 m²/g; said composition comprising from about 1 to about 99 percent by weight of a hydrogenating component comprising copper in elemental, hydroxide, carbonate, hydroxy-carbonate or oxide form and zinc oxide and incorporated therewith in inititum admixture from about 1 to about 30 percent by weight of silica substantially to increase the activity of the catalyst composition.

2. A composition according to claim 1 further characterized in that a pellet or extrusion made from said composition has a pore volume in the range of from about 0.2 cc/g to about 0.5 cc/g.

3. A composition according to claim 1 further characterized in that the crystals of said hydrogenating component have an average diameter less than about 70 angstroms.

4. A composition according to claim 1 further characterized in that said composition has an intrinsic surface area of from about 80 to 300 $m^2/g$.

5. A composition according to claim 1 further characterized in that said composition comprises from about 5 weight percent to about 20 weight percent of said silica component.

6. A composition according to claim 1 further characterized in that said hydrogenating component contains cobalt in elemental, hydroxide, carbonate, hydroxycarbonate or oxide form.

7. A catalyst composition having an intrinsic surface area of from about 110 to 200 $m^2/g$ comprising about 15 percent by weight of a silica component having an average particle diameter of from abut 3 nanometers to about 50 nanometers and about 85% by weight of a hydrogenating component consisting essentially of copper in elemental or oxide form, zinc oxde, and cobalt oxide wherein the crystals of said hydrogenating component have an average diameter less than 50 nanometers.

8. A catalyst composition having a BET intrinsic surface area above about 60 $m^2/g$ prepared by the method comprising the steps of:
(1) forming an aqueous solution of a water soluble salt of copper and zinc;
(2) adding a precipitating agent to the salt solution of step 1;
(3) separating the precipitate;
(4) mixing the precipitate with a silica component selected from the oxides of the element silicon, and water to form a heterogeneous mixture, wherein said silica component comprises from about 1 to about 25 weight percent of the total weight of said precipitate and said silica component; and
(5) heating the mixture from step (4) at a temperature of from about 100° C. to about 400° C. to dry and calcine the mixture.

9. A catalyst composition according to claim 8 prepared by the method further characterized in that said silica component has an average particle diameter ranging from about 3 nanometers to about 50 nanometers.

10. A catalyst composition according to claim 8 prepared by the method further characterized in that said silica component comprises from about 5 to 20 weight percent of the total weight of said precipitate and said silica component.

* * * * *

UNITED STATES PATENT AND TRADEMARK OFFICE
CERTIFICATE OF CORRECTION

PATENT NO. : 4,199,479
DATED : April 22, 1980
INVENTOR(S) : John B. Wilkes

It is certified that error appears in the above–identified patent and that said Letters Patent are hereby corrected as shown below:

Col. 4, line 7, "hydroxy carbonates" should read --different--.

Col. 11, line 5, "spirit" should read --split--.

Col. 14, line 34, "silica" should read --silica sol--.

Col. 15, line 19, "-Zb" should read -- -Zn --.

Signed and Sealed this

Seventh Day of October 1980

[SEAL]

Attest:

SIDNEY A. DIAMOND

Attesting Officer   Commissioner of Patents and Trademarks